(12) United States Patent
Barnes et al.

(10) Patent No.: US 10,188,792 B2
(45) Date of Patent: Jan. 29, 2019

(54) AUTOMATED PRESSURE LIMIT SETTING METHOD AND APPARATUS

(71) Applicant: CareFusion 303, Inc., San Diego, CA (US)

(72) Inventors: Erik Barnes, Solana Beach, CA (US); Robert Dwaine Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 213 days.

(21) Appl. No.: 14/882,338

(22) Filed: Oct. 13, 2015

(65) Prior Publication Data

US 2016/0030668 A1 Feb. 4, 2016

Related U.S. Application Data (62) Division of application No. 13/101,847, filed on May 5, 2011, now Pat. No. 9,612,023.

(51) Int. Cl.
*A61M 5/168* (2006.01)
*A61M 5/00* (2006.01)
*A61M 5/14* (2006.01)

(52) U.S. Cl.
CPC .......... *A61M 5/16854* (2013.01); *A61M 5/00* (2013.01); *A61M 5/1407* (2013.01); *A61M 2005/16863* (2013.01); *A61M 2005/16868* (2013.01); *A61M 2205/3334* (2013.01); *A61M 2205/3355* (2013.01); *A61M 2205/3362* (2013.01); *A61M 2205/3372* (2013.01); *A61M 2205/50* (2013.01); *A61M 2205/52* (2013.01);

(Continued)

(58) Field of Classification Search
CPC ......... A61M 2005/16863; A61M 2005/16868; A61M 2205/3334; A61M 2205/3355; A61M 2205/50; A61M 2205/52; A61M 5/16854

See application file for complete search history.

(56) References Cited

U.S. PATENT DOCUMENTS

| 4,743,228 A | 5/1988 | Butterfield |
| 5,803,917 A | 9/1998 | Butterfield et al. |

(Continued)

FOREIGN PATENT DOCUMENTS

| WO | 9804303 A1 | 2/1998 |
| WO | 2010096602 A1 | 8/2010 |
| WO | 2010129720 A2 | 11/2010 |

OTHER PUBLICATIONS

Extended European Search Report for Application No. 12779813.0, dated Jul. 17, 2015, 7 pages.

(Continued)

*Primary Examiner* — Deanna K Hall
(74) *Attorney, Agent, or Firm* — Morgan, Lewis & Bockius LLP (57) ABSTRACT

A method of infusing a fluid includes receiving values of one or more infusion parameters for an infusion of a fluid, Based on the received infusion parameter values, an occlusion pressure threshold for the infusion of the fluid is automatically calculated. During the infusion, a fluid pressure value is sensed. An indication is provided responsive to whether a value of the sensed fluid pressure is greater than the occlusion pressure threshold.

20 Claims, 7 Drawing Sheets

(52) U.S. Cl.
CPC ............... *A61M 2205/6054* (2013.01); *A61M 2205/6072* (2013.01)

(56) References Cited

U.S. PATENT DOCUMENTS

| | | | |
|---|---|---|---|
| 6,213,972 B1 * | 4/2001 | Butterfield | A61M 5/16859 604/67 |
| 8,387,662 B2 * | 3/2013 | Dykstra | E21B 34/08 137/813 |
| 2005/0145010 A1 | 7/2005 | Vanderveen et al. | |
| 2006/0135940 A1 | 6/2006 | Joshi | |

OTHER PUBLICATIONS

International Search Report and Written Opinion for PCT/US2012/034718, dated Nov. 26, 2012.
European Office Action for Application for Application No. 12779813.0, dated Dec. 21, 2017, 4 pages.

* cited by examiner

AUTOMATED PRESSURE LIMIT SETTING METHOD AND APPARATUS

CROSS-REFERENCES TO RELATED APPLICATIONS

This application is a divisional of U.S. patent application Ser. No. 13/101,847, entitled AUTOMATED PRESSURE LIMIT SETTING METHOD AND APPARATUS, filed on May 5, 2011, issued as U.S. Pat. No. 9,162,023 on Oct. 20, 2015, which is hereby incorporated by reference in its entirety for all purposes.

FIELD

The present disclosure is related to the field of infusion devices. Specifically, the present disclosure relates to arrangements and methods for automated calculations of occlusion alarm pressure thresholds used in controlling operation of an infusion device.

BACKGROUND

In medical care facilities, infusion of medical fluids into a patient is a commonly performed patient care operation. A fluid infusion device, such as an infusion pump, is typically configured to infuse a fluid from a fluid source into a patient through a vascular access device (VAD) such as a syringe or a catheter. If an occlusion occurs between the pump and the VAD, fluid does not reach the vascular system as intended and blood may back up resulting in clotting and attendant risks.

Prior to starting a fluid delivery session, a caregiver typically sets up the infusion device to alert the caregiver when fluid pressure in a infusion line exceeds a pressure threshold so that the caregiver could take corrective action to avoid possible harm to the patient. Current methods of setting up infusion devices include the caregiver entering a 'care area profile', e.g. NICU, for which the pressure limits and associated rules have been pre-configured. In some pumps, these pre-configured values may be adjusted by the caregiver while in other pumps the pre-configured values are fixed and all have limited ranges. Certain pumps are pre-configured to acquire a value during power-on, which the caregiver may or may not be allowed to control to adjust, though this acquired value is over a defined range of pressure values.

Caregivers may adjust pressure limits for several reason. For example, caregivers adjust pressure limits to minimize time to detection of an occlusion. This is important to avoid undue interruption of delivery of medication, to avoid exposure of the patient's vessels and tissue to a higher pressure than necessary and to avoid false alarms which would be issued due to occlusion, causing an interruption of medication delivery.

While mathematical formulae for calculating a pressure threshold are known in the art, caregivers typically select the pressure threshold for alarm based on their experience or using "rule of thumb" calculations. Often, caregivers do not have access to parameters such as catheter and tubing resistance, fluid viscosity and so forth, so caregivers often use preset values, perhaps based on the location of care or a flow rate. If the pressure threshold is set too low, then the fluid delivery equipment may frequently and unnecessarily alert the caregiver. Such false alarms take the caregiver's valuable time away from other medical tasks, interrupt flow of medication and elevate risk of clot formation in the VAD.

On the other hand, if the pressure threshold is too high, then increased fluid pressure may go unnoticed, thereby potentially harming the patient. Furthermore, a method sometimes used by caregivers is to set the pressure threshold simply to be a certain amount over the current pressure. This method may set the pressure threshold incorrectly high or low if the current pressure was erroneous, e.g., because there was an existing elevated pressure in the fluid line.

A more exact method for setting fluid pressure thresholds for alerting a healthcare professional when infusing a medical fluid into a patient is needed.

SUMMARY

In certain aspects of the present disclosure, a method of infusing a fluid is provided. The method includes receiving values of one or more infusion parameters for an infusion of a fluid. Based on the received infusion parameter values, a pressure threshold for the infusion of the fluid is calculated. During the infusion, fluid pressure is sensed. An indication is provided if a value of the sensed fluid pressure contravenes the occlusion pressure threshold.

In certain aspects of the present disclosure, a fluid pump includes a pressure sensor for sensing fluid pressure during an infusion of a fluid, a display, a memory and a processor. The processor is configured to receive values of one or more infusion parameters. The processor is also configured to calculate, based on the received infusion parameter values, an occlusion pressure threshold for the infusion of the fluid. The processor is also configured to receive, during the infusion, a fluid pressure signal from the pressure sensor. The processor is also configured to provide and indication responsive to whether a value of the received fluid pressure signal contravenes the pressure threshold.

In certain aspects of the present disclosure, a machine-readable medium encoded with instructions for performing an infusion of a fluid is provided. The instructions comprise code for receiving values of one or more infusion parameters. The instructions also comprise code for calculating, based on the received infusion parameter values, an occlusion pressure threshold for the infusion of the fluid. The instructions also comprise code for receiving, during the fluid infusion, a fluid pressure signal from a pressure sensor. The instructions also comprise code for providing an indication responsive to whether a value of the received fluid pressure signal contravenes the pressure threshold.

The foregoing and other features, aspects and advantages of the embodiments of the present disclosure will become more apparent from the following detailed description and accompanying drawings.

DETAILED DESCRIPTION

The disclosed arrangements and methods overcome the above discussed limitations, at least in part, by providing methods and systems for automatically calculating a occlusion pressure threshold for monitoring fluid pressure in an infusion fluid tube for alerting a caregiver.

Certain configurations of the present disclosure overcome the above limitations by providing a processor in a fluid infusion device configured to perform pressure threshold calculations based on infusion parameters obtained from a caregiver and/or communicating with other medical equipment. Using the infusion parameters, the processor calculates flow resistance due to the tubing and equipment used for the infusion. Flow resistance of the delivery fluid pathway, in conjunction with other measured and available parameters, is used in the computation of the occlusion pressure limit. In certain configurations, after the processor calculates a pressure threshold, the processor presents the calculated pressure threshold to a caregiver, obtains a confirmation or an alternate threshold value from the caregiver and monitors fluid line pressure of an ongoing infusion session based on the occlusion pressure threshold.

In certain configurations, the processor calculates a pressure threshold and monitors a multi-channel or a multi-segment infusion system. An occlusion pressure threshold is calculated by consideration of the "common" flows through all common segments of the infusion system, such as when multiple pumps infuse through a common catheter, as well as considering the fluid resistance of any intervening components and a fluid flow resistance of a vascular access device (e.g., a catheter) employed in the infusion system.

In certain embodiments, the pump computes the fluid flow resistance from data obtained by interaction with a user. If the user interface provides means to input a catheter type or model, the system stores pre-computed fluid flow resistance values for these devices. To calculate fluid flow resistance of a segment of infusion line, the processor uses infusion parameters such as the internal diameter (or bore) of the infusion line, the length of the fluid line and the viscosity of the fluid being infused. These and other infusion parameters are either input to the processor by a user or obtained by the processor from a database. Alternatively, the pump may dynamically measure the fluid resistance. In brief terms, this is performed by dynamically modulating the flow rate of the pump around the nominal flow rate programmed by a caregiver. For example, if the programmed flow rate is 100 ml/h, the instantaneous flow rate may vary by 10%. From measurements of pressure (dynamic changes) during these variations, the dynamic fluid flow resistance is computable in principle as the partial derivative of pressure with respect to the flow. U.S. Pat. No. 5,803,917 to Butterfield et al., the relevant portion of which is incorporated by reference herein, discloses some techniques for dynamic fluid resistance measurements.

In accordance with certain configurations, occlusion pressure threshold calculations are made by automatically identifying infusion connectors being used, obtaining flow resistance information for the identified infusion connectors from a database, optionally computing fluid flow resistance dynamically and calculating a working pressure in the fluid line. Once a working pressure is thus calculated, the occlusion pressure threshold for alarm is set to be a certain percent or a certain noise margin over the working pressure.

Figure 1:
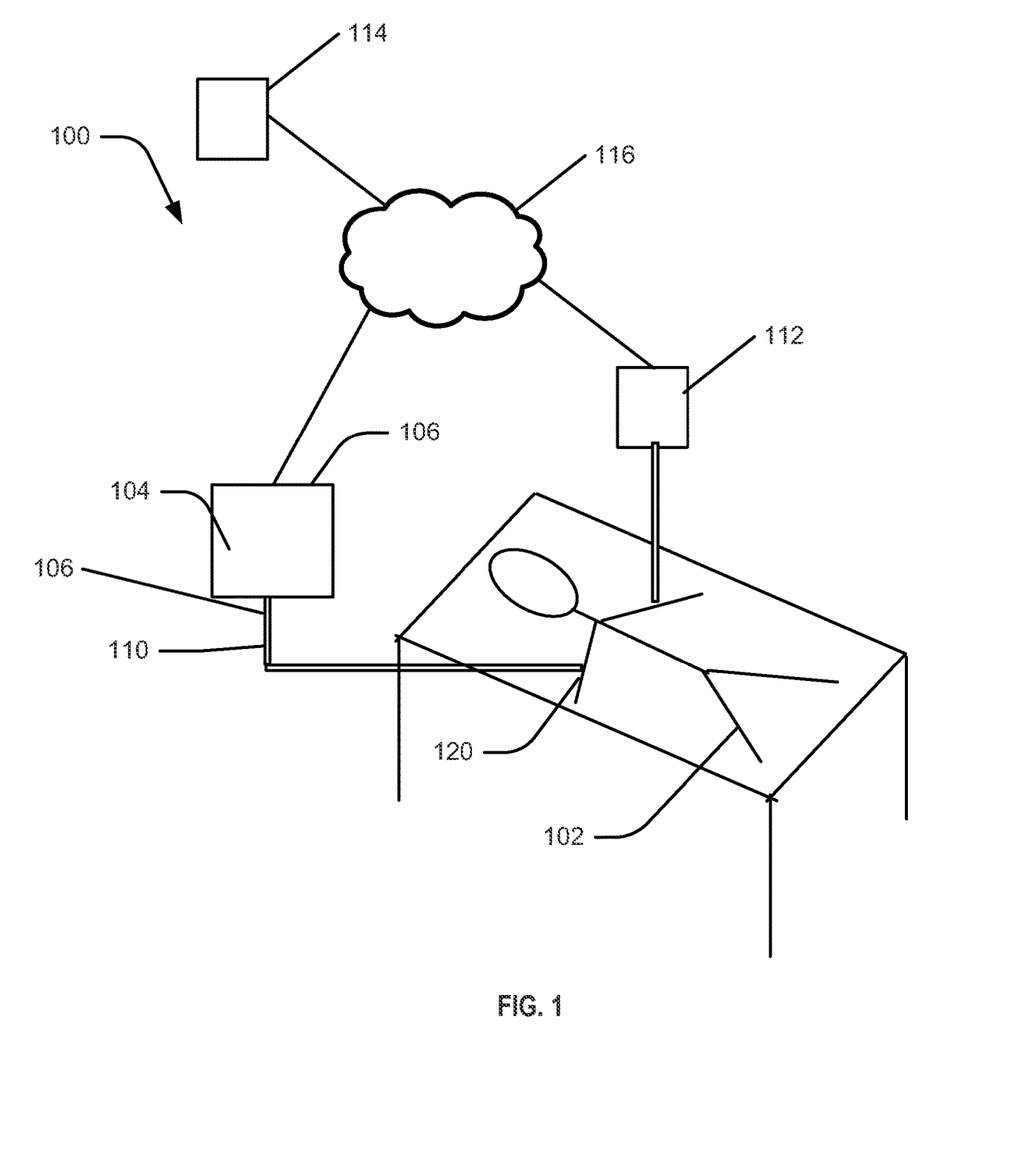
FIG. 1 is a block diagram representation of a patient care system, in accordance with certain configurations of the arrangement of apparatus according to the present disclosure.

FIG. 1 is a block diagram representation of a patient care system 100, in accordance with certain configurations of the present disclosure. A patient 102 is connected to a fluid delivery apparatus 104 for infusion of one or more fluids via vascular access device (VAD) 120 using a fluid line 110. In certain configurations the patient 102 is also be connected to an additional fluid delivery apparatus 112. The fluid delivery apparatus 104, 112 are communicatively coupled to a server 114 via a hospital network 116. The server 114 is configured to gather and provide information related to ongoing patient treatments in the hospital. In certain configurations, the server 114 is centrally located in a medical facility. In certain configurations, the server 114 is located at a caregiver's station. Other possible locations of the server 114 are also within the scope of the present disclosure.

Figure 2:
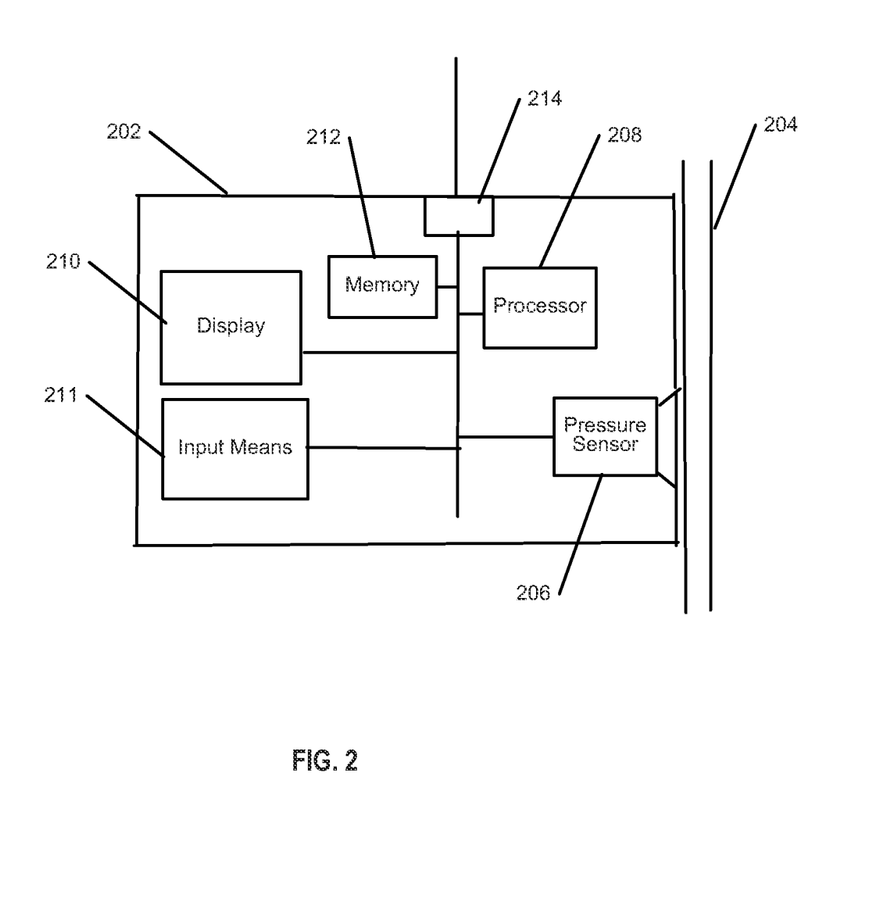
FIG. 2 is a block diagram representation of an infusion pump apparatus, in accordance with certain configurations according to the present disclosure.

FIG. 2 is a block diagram representation of a portion of the fluid delivery apparatus 104, in accordance with certain configurations. The fluid delivery apparatus 104 comprises a durable portion 202 and a disposable portion 204. A pressure sensor 206 is positioned on the durable portion 202. The pressure sensor 206 is configured to sense outflow fluid pressure in the disposable portion 204. The pressure sensor 206 is communicatively coupled to a processor 208 to provide sensed pressure readings to the processor 208. In certain configurations, the durable portion 202 is a modular fluid delivery system such as the ALARIS SYSTEM® infusion pump by CareFusion Inc. In certain configurations, the disposable portion 204 is a disposable IV set for attaching to an infusion pump such as a ALARIS SYSTEM® infusion pump.

Still referring to FIG. 2, the fluid delivery apparatus 104 further includes a display 210. The display 210 provides a user interface (e.g., text and/or graphics) for the processor to communicate with a user. In certain configurations, the display 204 is also an input device such as a touch-screen. The display 204 is communicatively coupled with the processor 208. The durable portion 202 also has one or more user input means 211 such as a keyboard, a barcode reader, a radio frequency identification (RFID) reader, and so on, as are well known in the art. A user can program infusion parameters or enter commands using user input means 211 to control the operation of the processor 208.

Still referring to FIG. 2, the processor 208 is further coupled to a memory 212. The memory 212 stores, for example, program code for execution by the processor 208, data used by the processor 208 for the pressure threshold calculations further described below, and so on. The processor 208 is also coupled to a communication module 214, which is configured to establish a communication link with the hospital network 116. The communication module 214 uses a wired or wireless communication technology such as the Ethernet or the IEEE 802.11 standard. In certain embodiments, the memory 212, is used to store a variety of data in a 'library' for use by the computation system. For instance, the memory 212 is programmed with the fluid resistance characteristics of the vascular access devices 120 and tubings (e.g., fluid lines 110) typically used in a hospital. Further, the memory 212 may contain subsets of these data aggregated by area of care—a so-called 'profile'—allowing automatic selection and presentation to the caregiver of only those devices used in that area along with other aspects of that care area. For instance, a profile for the Neonatal Intensive Care unit would contain the VAD's 120 and tubings 110 typical to that area and area-specific rules such as the 'noise margin pressure' to be applied in the computation of occlusion pressure limits. This 'noise margin pressure' accounts for, among other things, normal fluctuations of pressure due to anticipated movement, breathing, caregiver activity and similar which add to the pressure required to drive fluid through the resistance of the outflow pathway. It ALSO accounts for measurement uncertainty in the pressure sensor and BIAS due to hydrostatic pressure offset due to elevation differences between sensor and patient blood vessel.

Figure 3A:
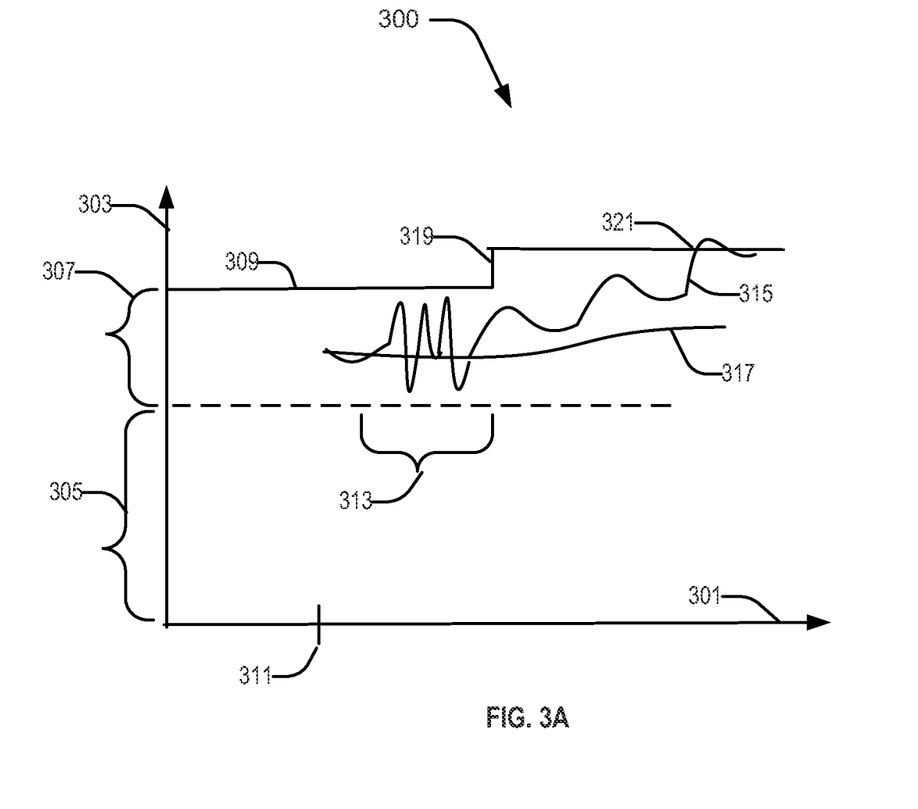
FIG. 3A is a graphical representation of an example of variations in fluid pressure as a function of time.

Referring to FIG. 3A, an example occlusion pressure limiting setting and monitoring operation of a fluid delivery apparatus 112 is explained next. FIG. 3A depicts a graphical representation 300 of fluid pressure (vertical axis 303) as a function of time (horizontal axis 301). Prior to starting a fluid infusion to a patient, the fluid delivery apparatus 112 calculates a working fluid pressure (reference number 305). As further explained below, the working fluid pressure is calculated from fluid delivery parameters of the tubings and connectors used, including length and the inner diameter, viscosity of the fluid to be delivered and flow rate. The fluid delivery apparatus 112 then calculates a "noise margin" 307 and adds the noise margin 307 to the working pressure 305 to arrive at a occlusion pressure threshold 309. The occlusion pressure threshold 309 represents an alarm limit so that during infusion, if fluid pressure sensed by the fluid delivery apparatus 112 (shown as curve 315) exceeds the occlusion pressure threshold (e.g., at time 321), then the fluid delivery apparatus 112 provides an indication.

In certain embodiments, the fluid delivery apparatus 112 also performs signal processing operations on the sensed fluid pressure (curve 315) to produce a processed sensed fluid pressure (represented by curve 317) and the above discussed indication may be provided when the processed sensed fluid pressure (curve 317) exceeds the occlusion pressure threshold 309. It will be appreciated by one of skill in the art that while FIG. 3 depicts situations where the occlusion pressure threshold is used to monitor whether a value of sensed fluid pressure exceeds the threshold, similar concepts are applicable to situations where a second pressure threshold is used to monitor the fluid pressure falling below the threshold value, such as, for example, when the VAD 120 inadvertently leaves a vein.

In certain embodiments, further explained in detail below, the fluid delivery apparatus 112 also adjusts the occlusion pressure threshold as a function of the sensed fluid pressure 315 (or 317). For example, if a certain patient's sensed fluid pressure 315 shows a certain amount of fluctuations (e.g., periodicity or intensity of pressure swings, as depicted in the time interval 313), the fluid delivery apparatus 112 changes the occlusion pressure threshold accordingly. In FIG. 3A, the occlusion pressure threshold is shown changed to a higher value (curve 319) after time period 313, in response to swings in the sensed fluid pressure during period 313.

Figure 3B:
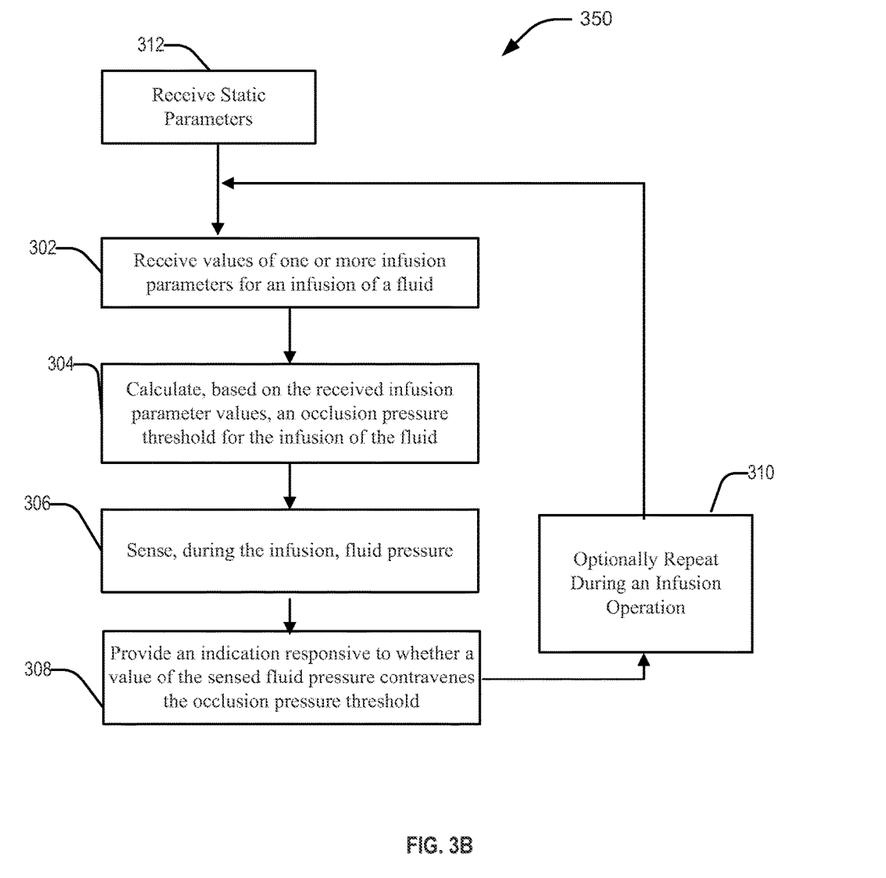
FIG. 3B is a flow chart representation of a method of infusing a fluid, in accordance with certain configurations according to the present disclosure.

FIG. 3B is a flow chart representation of a method 300 of infusing a fluid, in accordance with certain configurations. The method includes operation 302 wherein, the processor 208 receives values of one or more infusion parameters for an infusion of a fluid. As used herein, the term "infusion parameter" refers to one of several operational parameters that are used in fluid pressure calculations, including, but not limited to, information regarding type and dimensions of infusion equipment and tubings, clinical information about a patient, information about other ongoing infusions for the patient, information about fluid line topology (e.g., number of channels or manifolds), and so on. In some embodiments, as shown in box 312, before starting a patient infusion, "static" parameters such as patient weight, age, catheter type and location are entered and used in the initial computation of occlusion pressure limit along with "dynamic" parameters such as flowrate (e.g., as further described below with respect to box 310) are entered by a user and received at the processor 208.

Still referring to FIG. 3B and operation 302, in certain configurations, the processor 208 obtains one or more of the infusion parameters automatically; by wirelessly sensing (e.g., RFID) certain infusion equipment or by querying from another computer in communication with the hospital network 116, such as the server 114. In certain configurations, the processor 208 obtains the infusion parameters by prompting a user for manual entry of certain infusion parameters via, for example, the input means 211. In certain configurations, the processor 208 obtains the necessary infusion parameters using a combination of automatic and manual entries of the infusion parameters.

For example, in certain embodiments VADs 120 and tubings 110 may by divided into categories based on the flow resistance (e.g., a Reynolds number value). A marking (e.g., a barcode label or an RFID) is placed on the VAD 120 or the tubing 110, identifying the category of flow resistance. During the operation, the marking is read into the processor 208 manually or automatically, thereby allowing the processor 208 to perform the calculations described herein to determine the pressure thresholds discussed herein. In some embodiments, the flow characteristics are identified as a value directly usable by the processor 208. In some embodiments, the flow characteristics are identifies in terms of the physical dimensions and the processor 208 derives the working pressure values and thresholds, as further described below. Furthermore, in some embodiments, the processor 208 is provided with an identity of the fluid being pumped (e.g., fluid composition included 10% Dextrose and 8.5% lipid). As described in greater detail below, in some embodiments, the processor 208 uses fluid temperature signals received from a fluid temperature sensor to accurately determined viscosity of fluid being pumped.

Still referring to FIG. 3B and operation 302, in certain configurations, the processor 208 prompts a user to input information regarding the topology of the infusion system. For example, the processor 208 asks the user to input the number of channels used for infusion and configurations of any manifolds used. The processor 208 asks the user to input lengths of the fluid line segments upstream and downstream of the manifolds. The processor 208 further asks the user to input information related to a type of tubings and VADs used for infusion (e.g., a make/model identification of a catheter or a syringe). In certain configurations, the processor 208 displays a selectable list of tubings 110 and VADs 120 from which the user can select the tubings 120 and VADs 110 being used. Upon selection by the user, the processor 208 retrieves, from a database stored in the memory 212, information regarding the flow resistance of the tubings 120 and VAD 110 selected.

Still referring to FIG. 3B and operation 302, in certain configurations, the processor 208 asks the user for patient-specific information. The patient-specific information includes the patient's clinical profile including, for example, the patient's age, anticipated activity level, acuity to interruption of specific medication, etc. The patient-specific information further includes information about any other medical equipment currently connected to the patient, and associated facts. In certain configurations, the processor 208 prompts the user to input the identity of the patient, for example, by scanning the patient's wristband. Using the received patient identity, the processor 208 then obtains the patient-specific information needed for the calculation of the occlusion pressure threshold by communicating with the server 114.

Still referring to FIG. 3B and operation 302, in certain configurations, the processor 208 requests from the user, information regarding the fluid to be infused. In certain configurations, the processor 208 prompts the user to input the drug name and/or viscosity of the fluid solution being infused. In certain configurations, the processor 208 prompts the user to scan a barcode label attached to the drug vial, and then retrieves viscosity information from a drug database stored in the memory 212.

Still referring to FIG. 3B, the method 300 includes an operation 304 of calculating, based on the received infusion parameter values, an occlusion pressure threshold for the infusion of the fluid. The infusion parameters can be broadly divided into two categories, patient-dependent infusion parameters and patient-independent infusion parameters. The patient-dependent infusion parameters include a patient's clinical profile such as the patient's age and sensitivity to interruption of medication delivery. The patient-independent infusion parameters include parameters that affect the fluid mechanics of the infusion path, including flow rate, types and geometries of the fluid lines and connectors and viscosities of fluids being infused.

As indicated in Eq. (1) below, the alarm threshold pressure value is proportional to the product of the Flow_Rate and a resistance of the flow tubing, plus a NoiseMargin.

$$\text{Occlusion Pressure Limit} \propto \text{Flow\_Rate} * \text{Resistance} + \text{NoiseMargin} \quad (1)$$

The first component "Flow_Rate," in Eq. (1) above is generally patient-dependent and widely variable though in general increasing with patient weight. The second component "Resistance" is a quality of the fluid pathway dominantly influenced by the minimum tubing diameter and secondarily by the tubing path length as well as the viscosity of the fluid.

Still referring to FIG. 3B and operation 304, the processor 208 uses the flow rate and the resistance to determine the estimated 'working pressure' produced. In the case where there can be determined, such as via user input, that more than one pumping channel is infusing through a common lumen, the 'flow rate' will be the sum of the flows from each channel. To determine the occlusion pressure limit, the working pressure is computed and added to a 'NoiseMargin' which is required to accommodate for elevation differences when the patient may be higher than the pump, for venous pressure and for transient pressures produced by either physiology such as coughing, Valsalva or Mueller maneuvers and tubing movement during ambulation.

Still referring to FIG. 3B and operation 304, the processor 208 uses the flow rate of infusion to calculate the pressure threshold. In a typical medical infusion situation, the infusion flow rates are in the range where flows can be assumed to be laminar. Therefore, the well known Hagen-Poiseuille equation for cylindrical lumens can be used by the processor 208 in calculating the occlusion pressure threshold described by Eq. 1. If the processor 208 determines that the flow rate of the infusion is such that the Hagen-Poiseuille equation is not applicable, the processor 208 uses additional NoiseMargin to increase the pressure threshold. For example, the operation allowance is calculated using:

$$\text{Resistance} \equiv \frac{8 \cdot \mu \cdot L}{\pi \cdot d^4} \quad (2)$$

where:
$\mu$ is the dynamic viscosity of the fluid in Pascal-seconds
L is the length of the tubing channel in meters
d is the inner diameter of the tubing channel in meters The NoiseMargin partially depends on the patient and partially depends on other clinical information, further described below. The operational parameter is added to increase the NoiseMargin for an occlusion alarm threshold to reduce the possibility of false alarms. In certain configurations, the NoiseMargin depends on a patient's clinical profile. For example, if the patient is a child (e.g., in the neonatal unit), then a higher NoiseMargin value is used. Another example of the patient's clinical profile includes information related to the reason a drug is being infused. For example, certain drugs are infused at different flow rates, depending on the clinical reason for which the drug is being infused. For example, dopamine is infused at low levels for renal use, intermediate levels to increase cardiac output and blood pressure and high levels to increase vascular resistance. Therefore, in certain configurations, a lower NoiseMargin value is used when a particular drug is used for a particular clinical reason and where the programmed flow rate is low. For example, a lower NoiseMargin is used when dopamine is infused at low infusion rates since a quicker time to alarm is needed. This selection considers the potential for false alarms.

In some embodiments, the exact value of the dynamic fluid viscosity $\mu$ is determined using a temperature of the fluid as well as information as to the fluid type. The fluid temperature is obtained from, e.g., a signal received from a fluid temperature sensor.

In some embodiments, a technique of flow-rate-variable-filtering may be used to mitigate against false alarms at low flow. In this technique, the pressure sensor's signal is passed through a digital low-pass filter whose low-pass corner or cut-off frequency is a function of the flowrate. More specifically, the lowpass filter corner frequency is typically proportional to the flow rate so that as lower flow rates are used the filter acts to beneficially reduce the instantaneous rate of change of its output suppressing abrupt changes in pressure that may be causes by noise sources while responding with sufficient speed to detect an occlusion in a timely manner since the lower the flow, the slower the time-rate of increase of the pressure due to actual occlusion dynamics.

In certain configurations, the processor 208 is configured to generate an estimation of the time-to-alarm (TTA) value. The TTA value indicates to a caregiver an estimate of the time required to detect a full occlusion based on the present flow rate, pressure value, pressure limit and compliance of the tubing pathway as determined from inputs to the computer. The accuracy of this estimate is limited by the amount of information known e.g. the characteristics of all portions of the path may not be known. In some implementations, the system may dynamically estimate the compliance of the un-occluded system. The TTA is calculated using the following equation:

$$TTA = \frac{0.06 \cdot C \cdot PL}{FlowRate} \quad (3)$$

In Eq. (3), the variables are as follows.

C=infusion tube compliance in units of microliters/mmHg,

PL=pressure threshold limit to alarm (mmHg), and

Flow_Rate=flow rate in ml/hour.

TTA is time to alarm in minutes 0.06 is a conversion constant

This estimate of the TTA is presented to the caregiver to enable them to anticipate the impact of medication interruption should it occur and to, if desired, make overriding adjustments to the occlusion pressure limit set by the algorithm described.

Still referring to FIG. 3B and operation 304, if in operation 302, the processor 208 determines that the infusion configuration includes multiple channels and/or manifolded connectors, e.g., from the received inputs, then the processor 208 calculates the pressure threshold by taking into account the pressure drop in each of the manifolded tubes. The formula in Eq. (4) is used for calculating alarm threshold when multiple channels are used for fluid infusion.

$$\text{Occlusion Alarm Threshold} = \text{Resistance} \cdot \left( \sum_i \text{Flow Rate}_i \right) + \text{NoiseMargin} \quad (4)$$

In Eq. (4) above, the variable i is over all the flow rates in tubes 1 and 2. The processor 208 also calculates the NoiseMargin term in Eq. (4) as previously described herein. After the processor 208 has calculated each term, the sum of all the pressure values is used to determine the alarm threshold pressure value.

In some embodiments, the fluid flow path resistance might be measured using one of several well known techniques, omitted here for brevity.

Still referring to FIG. 3B, the method 300 further includes an operation 306 of sensing, during the infusion, a fluid pressure value. In certain configurations, the pressure sensor 206 senses the pressure of fluid in the disposable 204. In certain configurations, the processor 208 may perform a zero offset calculation (e.g., a baseline pressure to offset elevation difference between the fluid source and the patient). In certain configurations, the processor 208 samples pressure sensory measurements of the pressure sensor 206 at a predetermined frequency (e.g., 20 to 40 times per second). The pressure sensor 206 can use one of several well-known pressure sensing mechanisms such as a pressure sensing membrane, a piezo-electric element, and so on. In certain configurations, the processor 208 stores the sensed pressure data from the pressure sensor 206 in the memory 212. In certain configurations, the processor 208 performs data processing operations such as low pass filtering described in detail previously regarding the flowrate-variable-corner-frequency, noise removal and trend calculations on the sensed pressure data.

Still referring to FIG. 3B, the method 300 includes an operation 308 of indicating if the sensed and processed fluid pressure value contravenes the alarm threshold. The processor 208 periodically checks, by comparing the processed pressure data with the alarm threshold value, whether the measured fluid pressure contravenes the occlusion pressure threshold. Depending on the mode of operation, the contravening either indicates that the processed pressure data has fallen below a threshold value or is greater than an occlusion threshold value. For example, in certain embodiments, when the processor 208 determines that the processed fluid pressure has exceeded the occlusion alarm threshold, the processor 208 indicates this event to the user. In certain embodiments, when the processor 208 determines that the fluid pressure has dropped below an alarm threshold (e.g., because the VAD 120 has inadvertently left the vein), the processor 208 indicates this event to the user. In certain configurations, the mode of indication is pre-selected by the user from among various possible modes of indication. In one mode, the processor 208 alerts a user by issuing an audio alarm. In another mode, the processor 208 indicates the excess pressure event by flashing a light or an indicator on the display 210.

In another mode, the processor 208 transmits an alarm signal to the server 114, or another device (e.g., a computer at a caregiver station) communicatively connected to the processor 208. In yet another mode, the processor 208 pauses the fluid delivery. In certain configurations, the fluid delivery is resumed after the sensed pressure falls below the alarm threshold. In certain configurations, resumption of fluid delivery requires manual intervention by a caregiver. In certain configurations, a caregiver intervenes by communicating control messages to the processor 208 via the hospital network 116. In certain configurations, a caregiver can intervene using user input means 211 (e.g., keys on a front panel of the durable portion 202). The above modes may be separate or combined, such that, for example, an alarm and pausing of delivery may be performed together.

Still referring to FIG. 3B, in certain configurations, multiple alarm thresholds are used for indicating alarms of different degrees. For example, in certain configurations, a first alarm is indicated when the sensed fluid pressure is above a first (lower) alarm threshold and a second indication is issued if the sensed fluid pressure is above a second (higher) alarm threshold. For example, in certain configurations, the first alarm is an audible alarm while the second indication includes stopping the fluid delivery operation until manual intervention by a caregiver.

The process 350 depicted in FIG. 3B is recurrent in several possible ways, as indicated by box 310. For example, each time a parameter change is made, the occlusion pressure limit may be recomputed, for example, if the flow rate is changed, the occlusion pressure limit must be recomputed as indicated by Eq. (1). In an optional embodiment, the pump is able to continuously dynamically measure the actual fluid pathway flow resistance. Such a measurement involves multiple measures of pressure as the flow rate is instantaneously deliberately 'modulated' typically above and below the mean programmed flow rate and other comparable methods such as pressure pulse integration may be used. By continually measuring the flow resistance of the path, the pump is able to determine a more accurate occlusion pressure limit setting. Further, it may not require the entry of all parameters discussed above with respect to steps 312 and 310. In some use cases, these parameters may not be known thus the ability to determine the critical normal flow resistance assists in providing the automation of occlusion pressure limit setting.

Figure 3C:
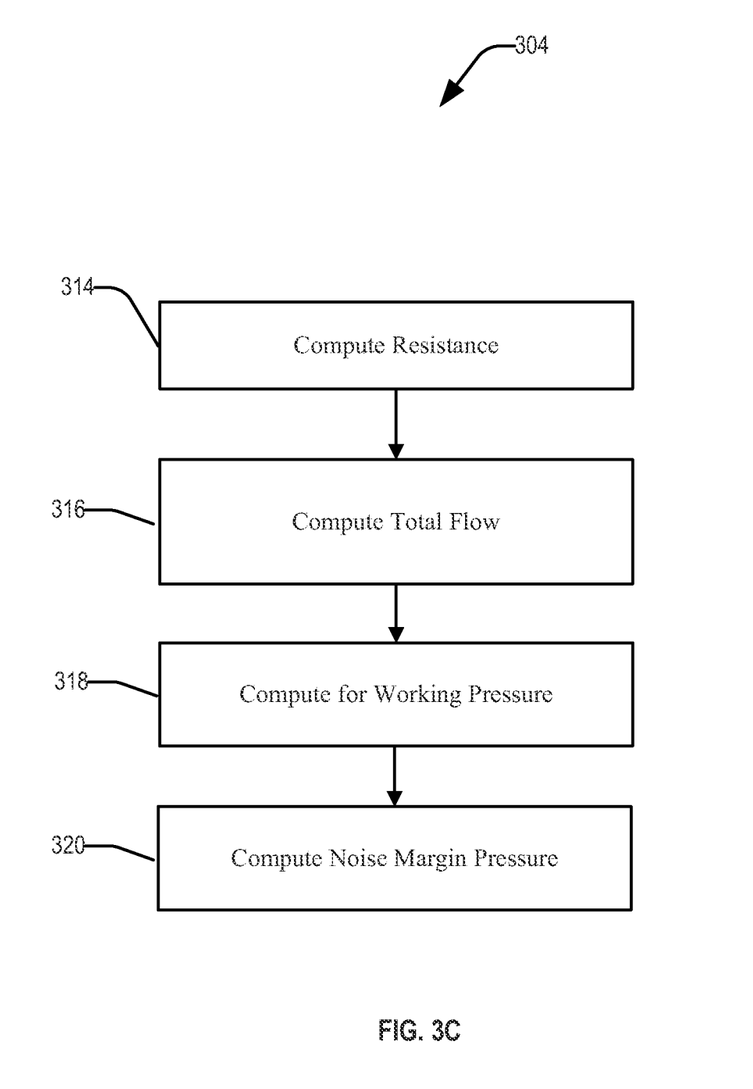
FIG. 3C is a flow chart representation of a method of calculating an occlusion pressure threshold, in accordance with certain configurations disclosed in the present disclosure.

With reference to FIG. 3C, the process of calculating the occlusion pressure threshold for the infusion of the fluid according to certain configurations is described below. At box 314, resistance of the fluid pathway used for an infusion operation is computed by the processor 208. The resistance is calculated, e.g., by computing Eq. (2) as previously described. At box 316, the total flow through a common infusion pathway, based on the configuration of the infusion system, is computed to calculate a theoretical working pressure for the entire infusion system. A working pressure value is calculated at box 318, using the previously described techniques. In step 320, noise margin pressure is computed, as previously described.

Figure 4:
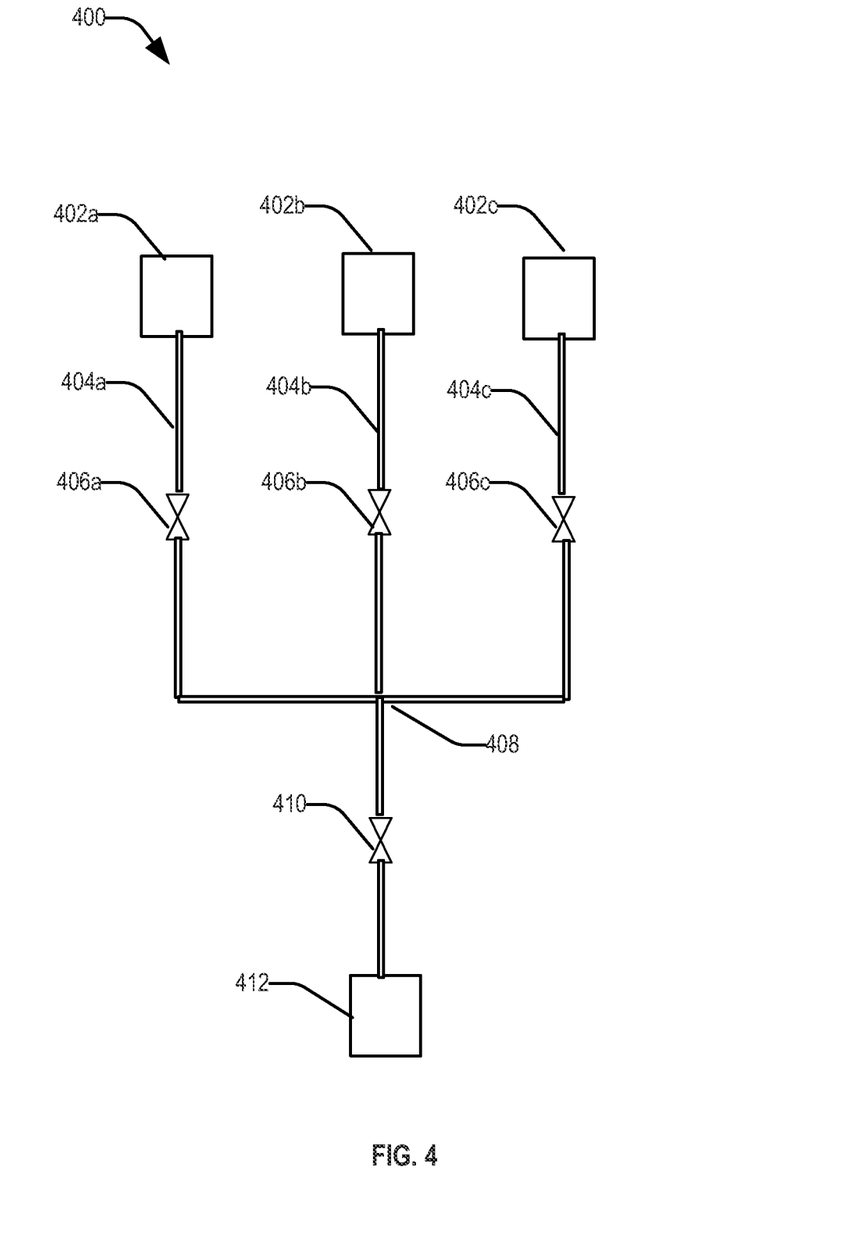
FIG. 4 is a block diagram representation of a multi-channel fluid delivery system, in accordance with certain configurations according to the present disclosure.

Referring now to FIG. 4, a block diagram representation of a multi-channel fluid delivery system in accordance with certain configurations disclosed in the present disclosure is depicted. Three fluid pumps 402a, 402b and 402c are connected through three fluid channel segments 404a, 404b, 404c having resistances 406a, 406b, 406c through manifold 408. The fluid line segment between manifold 408 and vascular access device 412 has a fluid resistance 410 and the VAD 412 has a resistance. As previously discussed, in certain configurations, where the topology of the infusion network is provided to the infusion system, the working pressure threshold can be computed using the following formula $$P_{working} = \sum_i Flow_i \cdot \sum_k Resistance_k \quad (5)$$

Where the "k" resistance values are comprised as follows:
R1=Resistance 406a in the fluid line section 404a
$R_{VAD}$=Resistance in the fluid line section 410
$R_{410}$=Resistance of the tubing 410 between the common connector 408 and the VAD 412, and the "i" flow values are comprised as follows:
$Flow_1$, $Flow_2$, $Flow_3$=Flow_Rate values for sections 404a, 404b and 404c, respectively.

Figure 5:
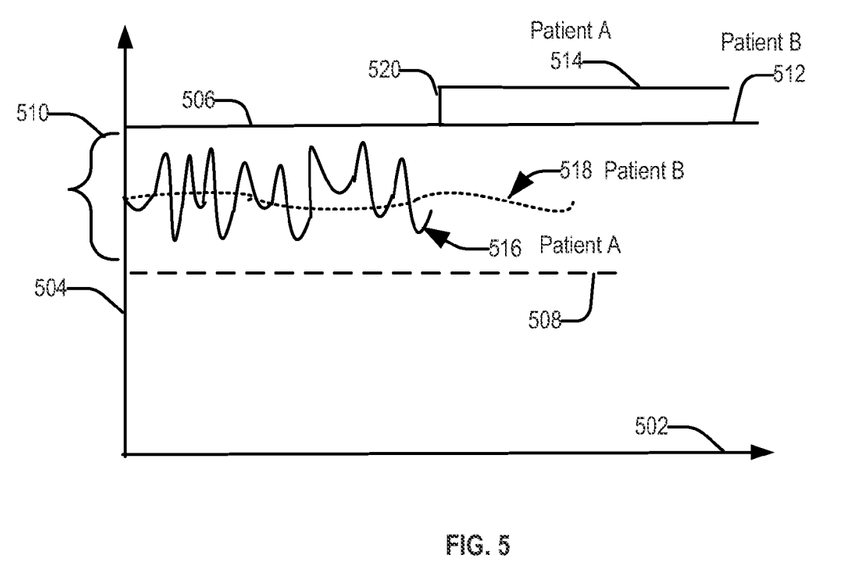
FIG. 5 is a graphical representation of fluid pressure changes as a function of time for two different patients.

Referring to FIG. 5, the real time adjustment of occlusion pressure threshold in certain embodiments is explained further. Fluid pressures sensed for two patients A and B are shown as curves 516 and 518 respectively, plotted along the horizontal axis 502 (time) and the vertical axis 504 (pressure). In the depicted example, at the onset of a fluid infusion, both patients A and B in this example are calculated to have the same theoretical fluid pressure (curve 508), the same noise margin (510) and therefore the same occlusion pressure 506. During infusion, the monitored fluid pressure of patient A is shown to have more fluctuations that the monitored fluid pressure for patient B. In some embodiments, patient A's occlusion pressure may be adjusted upwards (curve 514), while no change is made to patient B's occlusion pressure threshold (curve 512). Such a patient-specific adjustment to the occlusion pressure, in one aspect, helps mitigate the possibility of false alarm triggering. As previously discussed, the monitored fluid pressure for patients may be filtered with an appropriate lowpass filter (or Kalman filter) before making patient-specific adjustments to the occlusion pressure limits.

It will be appreciated that the methods and systems disclosed herein provide for automatic calculation and setting of pressure alarm thresholds for fluid pumps. In certain configurations, the alarm setting calculations are based on user input and/or automatically obtained information regarding connecting tubing geometries and a patient's clinical profile. The calculated alarm thresholds are used for alerting a caregiver to the presence of an occlusion by monitoring fluid pressure during an infusion session.

The automatic calculation of occlusion alarm thresholds, as provided by the present disclosure, improves the effectiveness of the occlusion alarm system by providing a threshold tuned to the specific conditions of the infusion rather than using a preset value or depending on general guidelines employed by the caregiver in manually operating the pump. Further in some embodiments the system is able to automatically adjust the occlusion pressure threshold during the course of the infusion session. This is achieved by the recomputation based on changing flow rates and, in one embodiment, by the continual measurement of the fluid pathway flow resistance.

It will further be appreciated that alarm thresholds can be automatically adapted to clinical conditions of a patient through communication between the fluid pump processor 208 and the hospital server 114. Such clinical conditions include, for example, the ward a patient is in, a patient's age, other ongoing infusions for the patient, and so on.

It will further be appreciated that, in certain configurations, the pressure threshold is programmed such that an 'alert' is issued upon detection of excess pressure, which then converts to a non-resetting alarm if the pressure fails to fall below a certain computed value such as a percentage of the alarm threshold in a defined period following the initiation of the alert state. In certain configurations, the pump operation is temporarily inhibited while the alarm and/or alert conditions exist.

It will further be appreciated that the automatic calculation of alarm thresholds disclosed herein therefore leads to better patient care by maintaining an optimized occlusion pressure limit that strikes a best balance between rapid detection and risk of false alarms.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A fluid pump, comprising:
a pressure sensor for sensing fluid pressure during an infusion of a fluid;
a display;
a memory; and
a processor coupled with the memory and the display, the memory storing program code that, when executed by the processor causes the processor to:
receive an identity of an infusion tubing connector or an infusion vascular access device used for the infusion of the fluid;
receive values of one or more infusion parameters;
calculate, based on the received identity and the received infusion parameter values, an occlusion pressure threshold for the infusion of the fluid;
receive, during the infusion, a fluid pressure signal from the pressure sensor; and
provide an indication responsive to whether a value of the received fluid pressure signal contravenes the occlusion pressure threshold.

2. The fluid pump of claim 1, wherein the stored program code, when executed by the processor, further causes the processor to:
calculate a theoretical working pressure value; and
add a noise margin pressure value to the theoretical working pressure value.

3. The fluid pump of claim 2, wherein, when executed by the processor, the program code causes the processor to calculate the theoretical working pressure value based on an amount of total flow infusing through a common infusion pathway, a flow resistance value of the common infusion pathway, and flow resistance values of any separate portions of the infusion pathway specific to a given pump.

4. The fluid pump of claim 2, wherein the stored program code, when executed by the processor, further causes the processor to:
receive patient identification information.

5. The fluid pump of claim 4, wherein the noise margin pressure value is calculated using the patient identification information.

6. The fluid pump of claim 1, wherein, when executed by the processor, the program code causes the processor to receive at least one value associated with the received values of the one or more infusion parameters from a database.

7. The fluid pump of claim 1, wherein, when executed by the processor, the program code causes the processor to receive the values of the one or more infusion parameters over a communication network from a server.

8. The fluid pump of claim 1, wherein the stored program code, when executed by the processor, further causes the processor to:
adjust, during the infusion of the fluid, the occlusion pressure threshold responsive to the sensed fluid pressure.

9. The fluid pump of claim 8, wherein, when executed by the processor, the program code causes the processor to adjust the occlusion pressure threshold responsive to a static operational parameter and a dynamic operational parameter.

10. The fluid pump of claim 9, wherein the static operational parameter comprises patient medical information.

11. The fluid pump of claim 10, wherein the dynamic operational parameter comprises statistical characteristics of the sensed fluid pressure.

12. A patient care system, comprising:
an infusion vascular access device;
an infusion tubing connector; and
a fluid pump fluidly configured to be fluidly coupled to the infusion vascular access device via the infusion tubing connector, the fluid pump comprising:
    a pressure sensor for sensing fluid pressure during an infusion of a fluid; and
    a processor; and
    memory storing program code that, when executed by the processor, causes the processor to:
        receive an identity of the infusion tubing connector or the infusion vascular access device;
        receive values of one or more infusion parameters;
        calculate, based on the received identity and the received infusion parameter values, an occlusion pressure threshold for the infusion of the fluid;
        receive, during the infusion, a fluid pressure signal from the pressure sensor; and
        provide an indication responsive to whether a value of the received fluid pressure signal contravenes the occlusion pressure threshold.

13. The patient care system of claim 12, wherein the fluid pump further comprises a display.

14. The patient care system of claim 13, wherein the stored program code, when executed by the processor, further causes the processor to operate the display to display a prompt to a user for manual entry of at least one of the values of the one or more infusion parameters.

15. The patient care system of claim 14, wherein the at least one of the values of the one or more infusion parameters comprises a number of channels used for the infusion.

16. The patient care system of claim 14, wherein the at least one of the values of the one or more infusion parameters comprises a configuration of a manifold.

17. The patient care system of claim 16, wherein the at least one of the values of the one or more infusion parameters further comprises a length of a fluid line segment upstream of the manifold.

18. The patient care system of claim 12, further comprising a server communicatively coupled to the fluid pump, wherein the stored program code, when executed by the processor, further causes the processor to receive at least one of the values of the one or more infusion parameters from the server.

19. The patient care system of claim 18, wherein the fluid pump further comprises an input device, wherein the stored program code, when executed by the processor, further causes the processor to receive at least an additional one of the values of the one or more infusion parameters from a user via the input device.

20. The patient care system of claim 12, wherein the memory further stores fluid resistance characteristics of the infusion vascular access device and the infusion tubing connector and storing a noise margin pressure to be applied in the calculation of the occlusion pressure threshold.

* * * * *